United States Patent [19]

Jastrzebski et al.

[11] 4,429,047

[45] Jan. 31, 1984

[54] METHOD FOR DETERMINING OXYGEN CONTENT IN SEMICONDUCTOR MATERIAL

[75] Inventors: Lubomir L. Jastrzebski, Plainsboro, N.J.; Jacek Lagowski, Woburn, Mass.

[73] Assignee: RCA Corporation, New York, N.Y.

[21] Appl. No.: 297,176

[22] Filed: Aug. 28, 1981

[51] Int. Cl.³ ............................................. G01N 21/35
[52] U.S. Cl. ........................................ 436/4; 436/136; 156/601
[58] Field of Search ....... 156/601, DIG. 64, DIG. 73, 156/DIG. 67; 436/4, 72, 136

[56] References Cited

U.S. PATENT DOCUMENTS 4,344,815  8/1982  Cazarra et al. ...................... 156/601

OTHER PUBLICATIONS

Katz, J. Electrochem. Soc.: Solid-State Science and Technology, Jul. 1978, pp. 1151–1155.
ASTM Standards, Part 43-Electronics, The Standard Designation: F 120-75, entitled "Infrared Absorption Analysis of Impurities in Single Crystal Semiconductor Materials."
ANSI/ASTM F 121-79, entitled "Standard Test Method for Interstitial Atomic Oxygen Content of Silicon by Infrared Analysis."
S. M. Hu, J. of Appl. Physics, 51 (11), Nov. 1980, entitled "Infrared Absorption Spectra of SiO₂ Precipitates of Various Shapes in Silicon: Calculated and Experimental," pp. 8945–5948.
K. Tempelhoff, et al., Phys. Stat. Solidi, (a) 56, 213 (1979), pp. 213–223, entitled "Precipitation of Oxygen in Dislocation-Free Silicon."
E. M. Ryzhkova, et al., Sov. Phys. Semicond., entitled "Optical Properties of Oxygen in Silicon," vol. 11, No. 6, Jun. 1977, pp. 628–630.

Primary Examiner—Hiram H. Bernstein
Attorney, Agent, or Firm—Birgit E. Morris; Donald S. Cohen; Joseph D. Lazar

[57] ABSTRACT

The content of oxygen, if any, that is present in a body of essentially monocrystalline semiconductor material is determined by converting by heating all of the oxygen in the body to interstitial form. The oxygen content is measured by infrared beam evaluation of the absorption band to identify the interstitial oxygen present in the material.

11 Claims, 7 Drawing Figures

METHOD FOR DETERMINING OXYGEN CONTENT IN SEMICONDUCTOR MATERIAL

This invention relates to a method for determining the oxygen content of semiconductor material and more particularly, the oxygen content in a body of monocrystalline semiconductor material.

BACKGROUND OF THE INVENTION

The presence of oxygen as a major impurity in grown silicon is well known. The oxygen in Czochralski (CZ) grown silicon, for example, is normally present in an amount greatly exceeding the room temperature solubility limit. Thus, it is incorporated into the CZ silicon lattice in various aggregated forms, i.e. precipitates or complexes of oxygen and silicon. The effect of the various forms of noninterstitial oxygen on the properties of silicon is complex. Some of the noninterstitial oxygen, thought to be incorporated as complexes, is known to improve the mechanical strength of silicon wafers which increases wafer resistance to warpage. Other noninterstitial oxygen, thought to be incorporated in CZ silicon as precipitates can introduce dislocations and reduce the mechanical strength of the silicon. Furthermore, precipitates of this type associated with stacking faults in the region of the semiconductor device (the substrate surface region) are detrimental to electrical performance. However, these same defects can improve electrical performance if, as gettering sites, the oxygen related defects are outside the device region, i.e. in the interior of the silicon wafer.

Gettering by oxygen precipitates is a widely used procedure for which, in each device fabrication procedure, an optimum size, concentration and spatial distribution of oxygen precipitates exists. The generation of the gettering precipitates, i.e. the precipitation kinetics of oxygen in silicon, depends on the concentration of the interstitial oxygen, carbon and, as has been shown indirectly, on the amount of initially precipitated oxygen in as-grown wafers.

Thus, to achieve reproducible oxygen precipitation during device fabrication, the amount of oxygen in precipitates and complexes in the virgin wafers should be measured in addition to monitoring carbon and interstitial oxygen concentration.

Techniques for determining the oxygen content of semiconductor materials such as silicon are well known. Some of them are destructive to the material to be analyzed and others are not. One example is by irradiation of the silicon as by $He^3$ ions to cause a nuclear reaction with oxygen that can be used to determine oxygen content by measuring the decay product. Another example is the flame fusion technique by which the silicon is evaporated and by emission spectroscopy one can determine the oxygen content in the silicon that has been evaporated. Still another example is known as the secondary ion mass spectroscopy technique. Another technique for determining oxygen content is what may be termed wet chemical analysis by which the silicon is dissolved in a chemical which causes disassociation of the silicon and other material contents causing oxygen to be separated from the other materials. By calorimetric techniques one can determine the oxygen that was present in the material prior to the solution melt that was developed.

In all of the known techniques outlined above, the accuracy and sensitivity of the measurements are not all that is desired. Moreover, those techniques which cause destruction of the material are obviously not desirable with certain IC processing. Furthermore, most of these techniques require certain kinds of equipment and procedures that are cumbersome and difficult to utilize in conventional IC processing facilities.

In the art of IC processing, particularly using silicon material, it is known how to determine the oxygen content existing in one or more forms of oxygen. For example, the techiques for determining oxygen in interstitial positions within the crystalline lattice structure is well known as described in the ASTM Standards, Part 43-Electronics, published by the American Society for Testing and Materials, the Standard Designation:F 120-75, entitled "Infrared Absorption Analysis of Impurities in Single Crystal Semiconductor Materials," and ANSI/ASTM F 121-79, entitled "Standard Test Method for Interstitial Atomic Oxygen Content of Silicon by Infrared Absorption." Reference is made to the article cited on page 2 of the latter test method by W. Kaiser and P. H. Keck, entitled "Oxygen Content of Silicon Single Crystals," published in the *J. of Appl. Physics*, Vol. 28, 1957, p. 882, for a more detailed explanation of the method of the ASTM Standards.

Moreover, it is known how to determine some forms of precipitated oxygen in silicon crystals as described, for example, by S. M. Hu in the *J. of Appl. Physics*, 51 (11), November 1980, pp. 8945–5948. See also the paper entitled "Precipitation of Oxygen in Dislocation-Free Silicon" by K. Tempelhoff, et al., *Physica Status Solidi*, (a) 56, 213, (1979), pp. 213–223 for a description of additional absorption bands related to absorption by oxygen precipitates. Also see "Optical Properties of Oxygen in Silicon" by Ryzhkova, et al., *Sov. Phys. Semicond.*, Vol. 11, No. 6, June 1977, pp. 628–630 for a description of studies of heat treatment effects of silicon on the absorption spectra of oxygen.

Furthermore, techniques are known for determining substitutional oxygen in silicon as described in a paper entitled "ACTIVATION OF THE OXYGEN DONOR IN Si ON A MICROSCALE," by P. Rava, H. C. Gatos and J. Lagowski, published in *Semiconductor Silicon*, 1981, The Electrochemical Society Inc. (Softbound Conference Series) (1981), pp. 232–243. However, there is nothing in the prior art known to us that teaches or suggests how to determine forms of oxygen precipitates or complexes other than that described above by S. M. Hu or Ryzhkova, et al.

It is clear that there is nothing in the art that teaches a simple, nondestructive technique that is both accurate and sensitive to determine the total oxygen content in semiconductor material.

SUMMARY OF THE INVENTION

According to the present invention, the total oxygen content in a body of essentially monocrystalline semiconductor material is determined by measuring the intensity of the absorption band related to the interstitial oxygen of said material to provide an intensity signal representing the total interstitial oxygen of the material. The body is prepared for such measurement by converting all of the oxygen in said body into the interstitial form by appropriate heating and cooling. The precipitate forms of oxygen in the body may also be determined by first measuring the content of oxygen in interstitial form prior to heating the body and thereafter determining the total oxygen content in the body and comparing the two values.

DETAILED DESCRIPTION OF A PREFERRED EMBODIMENT

Figure 1:
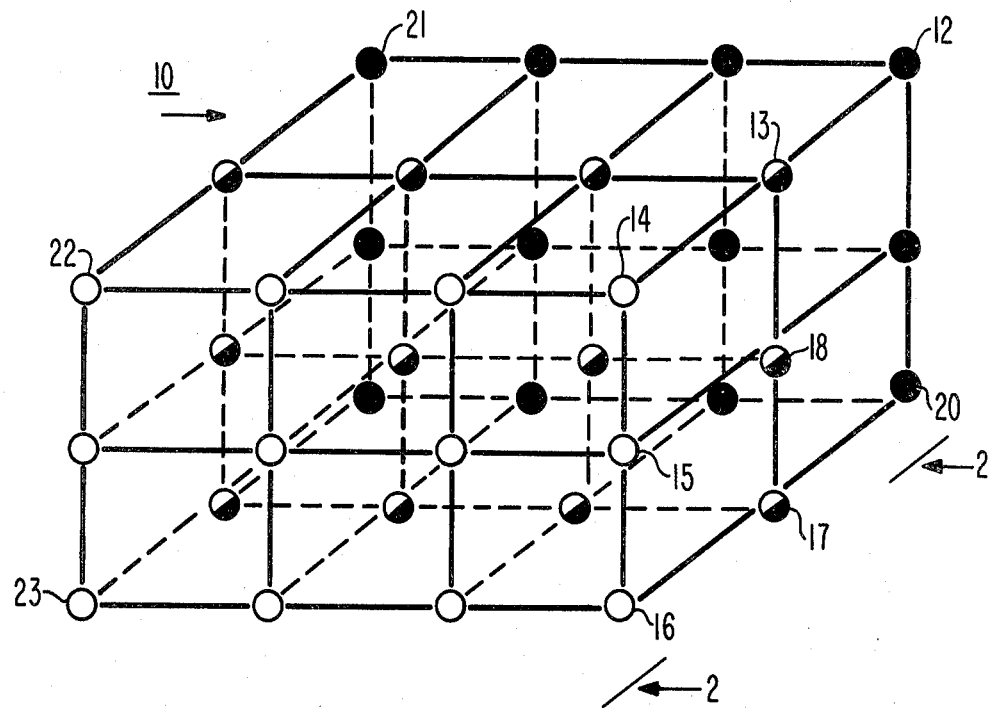
FIG. 1 is a diagram of a typical semiconductor lattice of the form well-known in the art to illustrate the principles of the present invention.
Figure 2:
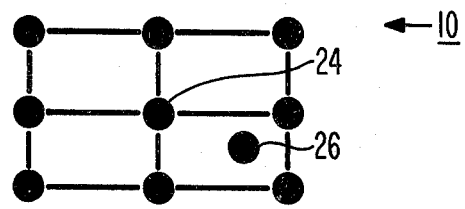
FIG. 2 is an end view of the lattice illustrated in FIG. 1 as seen along viewing plane 2—2.

The semiconductor lattice 10, as illustrated in FIG. 1, comprises, for example, silicon at positions 12, 13, 14–23 ... etc., of such a lattice. If one of the silicon atoms is replaced by an impurity such as a metal, the lattice is modified as indicated in FIG. 2 by a substitutional impurity 24. This position of substitution may occur anywhere in the lattice and could be, for example, position 18, of FIG. 1. If an atom is not within the corners of the lattice but is positioned between the corners of the lattice, then the position is known as an interstitial position as represented by position 26 in FIG. 2. This position 26 can occur anywhere within the lattice 10 provided it is within one of the intersection points of the crystalline structure.

For this description of the invention it will be understood that the single atoms of oxygen that are caused to be positioned at nonintersecting portions of the crystalline lattice will exist at an interstitial location such as position 26 of FIG. 2. Such locations shall be the sites for interstitial oxygen. Oxygen forms that are positioned at the intersections of the lattice such as position 24 shall be designated substitutional oxygen forms.

Oxygen atoms which are in interstitial or substitutional positions and situated so close to each other that they interact with each other will be referred to as an oxygen complex. An oxygen precipitate is such an oxygen complex having a well defined crystallographic structure different from the crystallographic structure of the host semiconductor lattice. Oxygen which occurs in substitutional, precipitate, or complex form shall be collectively referred to as noninterstitial oxygen.

Figure 3:
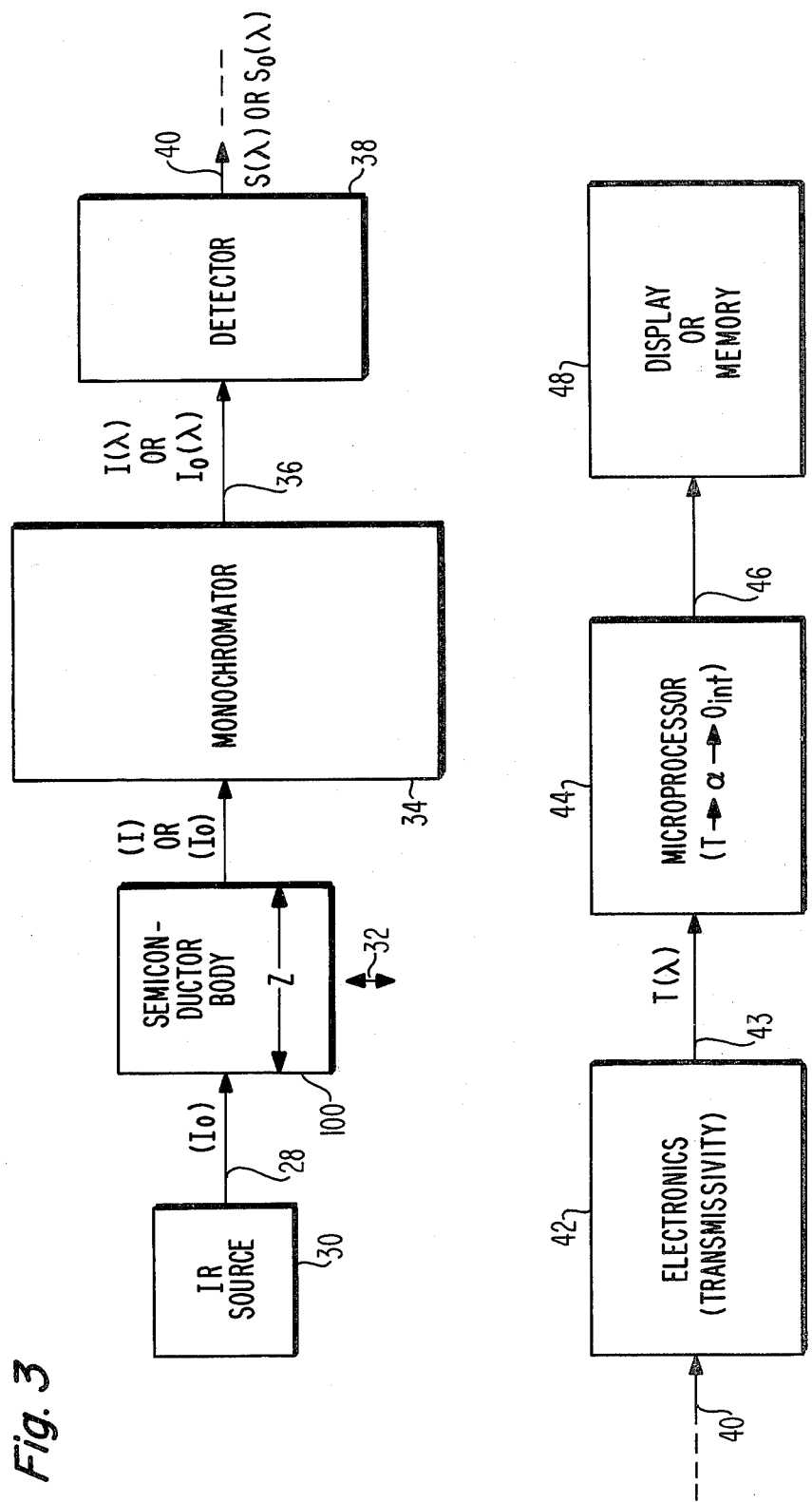
FIG. 3 is a simplified block diagram of the components of a system for making the measurements for determining the oxygen content of a semiconductor material according to the invention.

Reference is now made to FIG. 3, illustrating in block schematic form a system for the determination of the oxygen content in a body of semiconductor material. In general, the material of a body must be essentially monocrystalline and capable of containing interstitial oxygen that can be identified by a well-defined absorption band in response to electromagnetic energy, such as an infrared beam. A sample or specimen body 100 of semiconductor material that has been suitably prepared, as will be explained, is positioned to receive a beam 28 from an IR source 30. The sample body 100 is suitably mounted and arranged to be moved back and forth as indicated by arrows 32 to allow the beam 28 to pass through the sample or to pass directly to a monochromator 34. The intensity of the incident beam 28 of IR energy shall be represented by $I_0$. The intensity of the beam that has been transmitted through the body 100 is represented by I. The IR beam 28 formed of a relatively broad spectrum of wavelengths of energy is converted by the monochromator 34 to a beam at a predetermined wavelength $\lambda$. In the practice of the invention using silicon, for example, the wavelength $\lambda$ is 9.04 $\mu$m, or, conveniently, 9.0 $\mu$m.

The monochromator 34 may be any suitable apparatus known in the art to provide a monochromatic optical output beam of preselected wavelength in response to an input infrared beam of wide spectrum. The monochromatic optical output beam 36 from the monochromator 34 is applied to a detector 38 for generating an electrical intensity signal S or $S_0$ where S is derived from I and $S_0$ from $I_0$, sometimes represented as $S<->I$ and $S_0<->I_0$. The output of the detector 38 is applied via path 40 to suitable electronics 42 arranged to determine the transmissivity T of the body 100 responding to the IR beam 28 by dividing S by $S_0$. The transmissivity T is the ratio of the transmitted beam intensity, I, which corresponds to signal, S, to the incident beam intensity, $I_0$, which corresponds to Signal $S_0$. A signal representing this ratio T is applied via path 43 to a microprocessor 44 which computes the absorption coefficient $\alpha$ and the oxygen concentration $O_{int}$. The interstitial oxygen concentration $O_{int}$ is determined in accordance with the guidelines of the ASTM method showing the equations for converting oxygen concentration from the absorption coefficient ($\alpha$). A signal representing the oxygen concentration $O_{int}$ is applied via path 46 to a suitable display or memory 48 such as a chart recorder, a CRT, or, if desired, a suitable memory to store the information for later use.

The relationship of the various parameters that are determined and calculated by the system may be approximately represented by the following relationship: (when multireflections can be ignored)

$$T=(I/I_0)\simeq(1-R)^2 \exp{-\alpha z} \tag{1}$$

where T is the transmissivity as explained above; R is the reflection coefficient of the body 100 to the beam at the first external surface and the second internal surface of the body; exp is the mathematic constant e; $\alpha$ is the absorption coefficient of the material to the electromagnetic radiation; and z is the thickness of the body 100 as indicated in FIG. 3.

Before explaining the operation of the apparatus to make the measurements for the determination of the oxygen content in the body 100, a description will now be made of how to prepare the body 100 for the measurements. A sample body 100 of a known form of semiconductor material is heated to a predetermined temperature sufficient to convert all oxygen present in the body to interstitial form so that, all of the oxygen will be in interstitial position such as position 26 illustrated in FIG. 2. The sample body 100 is thereafter cooled to a lower predetermined temperature at a certain rate of cooling to maintain all of the oxygen in the interstitial form or positions. The manner of determining, respectively, the predetermined heating temperature and the predetermined cooling temperature will be explained in detail hereinafter, particularly with reference to the curve plots shown in FIGS. 5, 6 and 7.

Thereafter, the surface of the sample body 100 is preferably treated to make it a substantially homogenous in oxygen distribution with a defect free surface. The surface, for example, is prepared by stripping off any surface oxide that may have developed during the heating of the body 100 with a hydrofluoric acid (HF) solution. The surface of the body may then be lapped to remove about a 40 μm layer. This material is removed to obviate the presence of any oxygen that may have been sublimated from the interior of the body to both surface layers during the heating processing. Such oxygen is called in some literature "oxygen outdiffusion." Thereafter, the surface may be polished using, for example, colloidal silica. The surface treatment just outlined has been found to be reliable and satisfactory in preparing the body surface to be defect free for irradiation and having the body itself thereby to be substantially homogenous in the oxygen distribution. Nevertheless, if the body is tested without such treatment, the results may be less accurate because the surface layer is depleted in oxygen.

It should be understood that the principle of the invention requires that the crystallographic structure of the material be monocrystalline and capable of containing interstitial oxygen, which must be capable of providing an absorption band. Moreover, such material can be polycrystalline, but, nevertheless, essentially monocrystalline in form.

The embodiment being described is based on the use of commercially available [100] oriented, 3" and 4" diameter, Czochralski grown silicon wafers. Other forms of semiconductor material may also be used in the practice of the invention. Such other materials include germanium provided such material is essentially a monocrystalline lattice and is capable of containing interstitial oxygen.

Gallium arsenide, although capable of supporting interstitial oxygen, does not appear to provide an absorption band of the interstitial oxygen for reasons that are not entirely clear to us. Nevertheless, the invention can be used for any material that will provide an absorption band for insterstitial oxygen, silicon, and germanium being the only materials presently known to us having those requisite properties.

In order to determine the temperature at which the body of semiconductor material must be heated to convert all of the oxygen to interstitial form, a sample of the material representing the samples to be tested is heated to a certain minimum temperature and cooled to another but lower temperature at a rate that maintains the oxygen in interstitial form. The interstitial oxygen concentration of the specimen is measured by the apparatus of FIG. 3. Four different specimens from the same wafer were so heated as indicated by the plotted points shown in FIG. 5. Thus, at plot location 50, four specimens represented by the four different symbols were heated to a temperature of 1200° for one hour. Thereafter, cooling to a temperature of about 400°, at a rate of 30° C./min was sufficient to maintain the oxygen in interstitial form and thereby prevent precipitation of the oxygen. Several such measurements were taken at 1250° to produce plots at location 52 and at 1300° for plot location 54 and at 1350° for plot location 56. Measurement was also made at 1370° C. to assure that the maximum effect of heating had been reached. Accordingly, it is seen from the resulting curve 51 of the heating temperature versus oxygen concentration, that saturation occurs at 1300° for a silicon material.

Similar calibration curves must be generated for each different kind of semiconductor material that is to be tested. What has been discovered by experimental tests is that silicon material, regardless of the manner in which it is made, may have a saturation temperature that starts at a temperature lower than 1300°. Nevertheless, as a general guideline, if a semiconductor material formed of silicon is heated to a temperature of 1300°, it will most likely convert all oxygen into interstitial form.

Figure 6:
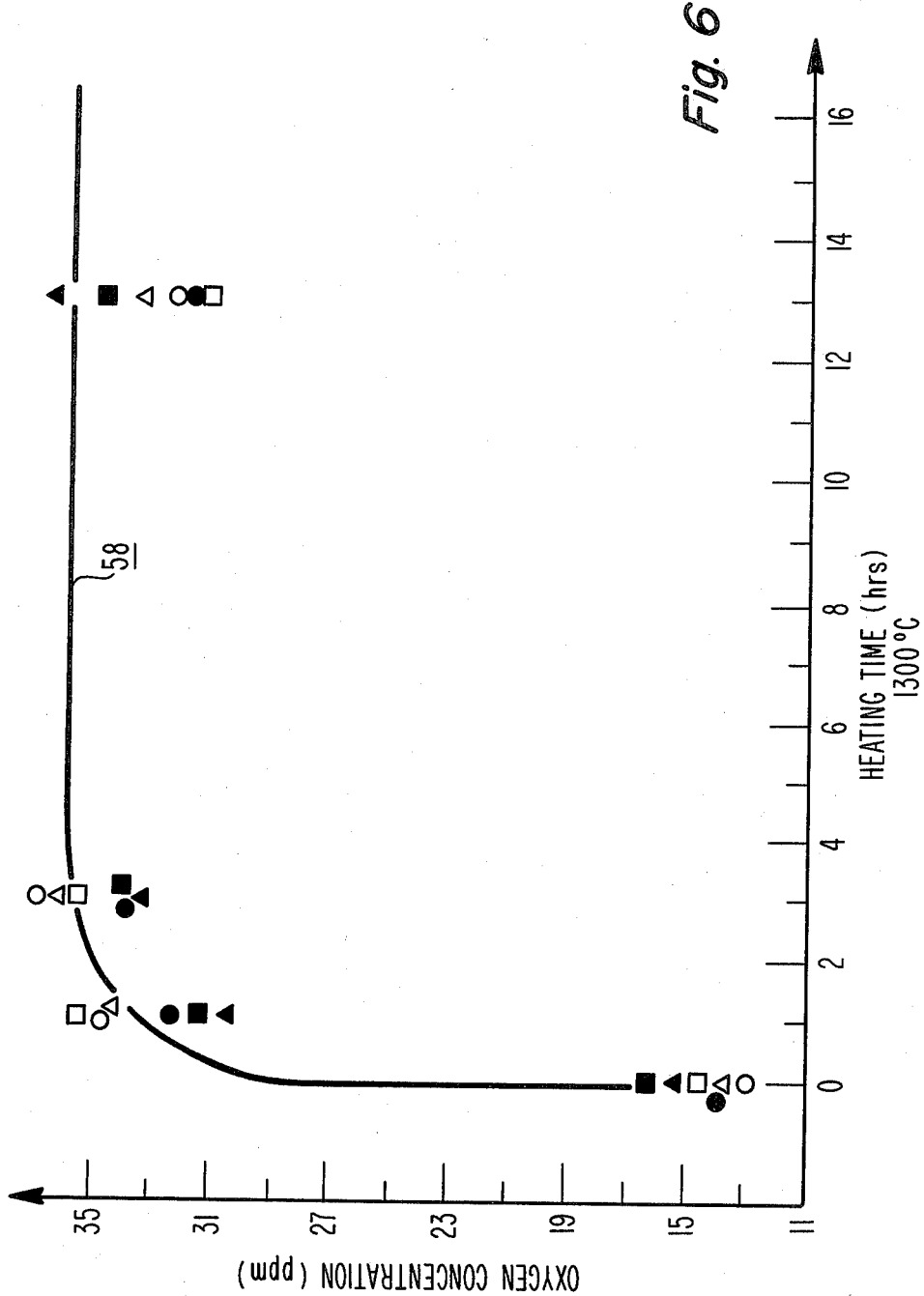
FIG. 6 is a curve plot to illustrate the heating time required to convert the oxygen in a semiconductor material to interstitial form at 1300° C.

FIG. 6 illustrates a plot of experiments on the same wafers but of different portions thereof to determine the minimum heating time necessary to convert the oxygen concentration into interstitial form. It appears that the heating time of about one hour is adequate to achieve the conversion of oxygen into interstitial states. Any time greater than one hour does not affect the conversion.

Figure 7:
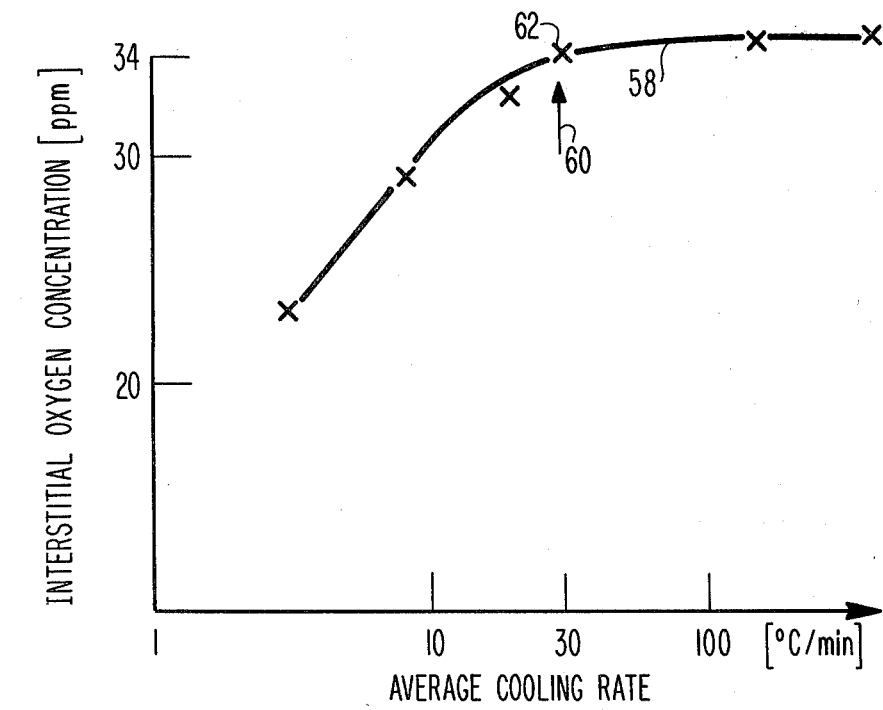
FIG. 7 is a curve plot to illustrate how to determine the average cooling rate after heating the material.

FIG. 7 illustrates a plot of a typical experiment using specimens from the same wafer of a given material to determine the minimum cooling rate to maintain the position of interstitial oxygen. The tests are performed on a series (here six) of specimens taken from a given wafer of silicon. Each specimen is heated to 1300° C. for one hour as described above. The material is cooled at the different respective rates indicated in FIG. 7 for each of the six test specimens. The cooling rate for each instance is merely an average of the temperature that was used. The interstitial oxygen was then measured as described above to provide the values indicated on FIG. 7. It was determined for this plot that the minimum cooling rate is about 30° C./min. as indicated by the knee of the curve 58 shown by arrow 60. This critical cooling rate corresponded to test sample point 62 showing that 34 ppm of interstitial oxygen existed after cooling from 1300° C. to 400° C. at 30° C./min. While the minimum cooling rate needed to maintain the oxygen in the interstitial positions in the lattice is determined from a such a curve plot, we have found that the cooling temperature range between 1100° C. and 650° C. is critically important. Within this temperature range the minimum cooling rate must be strictly followed, otherwise precipitation of oxygen from the interstitial positions may take place. It seems that the cooling rates between 1300° to 1100° and 650° to 400° C. are not as critical in this regard. Other specimens of semiconductor material will require different ranges of temperature to be determined in a similar manner.

Figure 5:
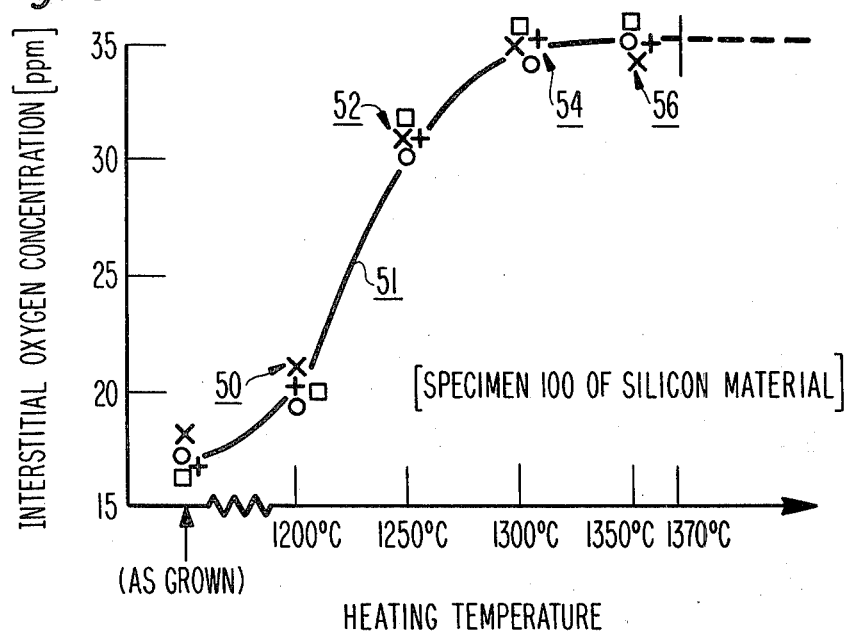
FIG. 5 is a curve plot of the heating temperature and the resultant interstitial oxygen concentration that results from the heat treating of silicon material.

It should be understood that the manner of determining the minimum critical heating temperature in accordance with FIG. 5, described above, is preferably done for each form of semiconductor material that is to be tested. In practice, a wafer from a boule of semiconductor material or a portion of the boule material is tested for the critical temperatures and cooling rate, etc. The critical temperature as shown in FIG. 5 and the heating time as shown in FIG. 6 are determined independently of the cooling rate as shown in FIG. 7. The respective parameters are determined in an iterative manner, as will be apparent to those skilled in the art.

The mechanism of the conversion of the oxygen to interstitial form in response to the heating is caused by the decomposition of oxygen precipitates that may exist in the body of semiconductor material. At high temperatures, such as 1300° C. for silicon, when the concentration of dissolved oxygen is below the solid solubility limit, the disassociation of oxygen precipitates will take place. Oxygen derived from such precipitates will be incorporated into the silicon lattice 10 as an interstitial substituent as, for example, in position 26 of the lattice 10 illustrated in FIG. 2. During what is essentially rapid cooling of the heated body to room or ambient temperature the oxygen remains frozen in the silicon lattice 10, not having enough time to precipitate when its concentration exceeds the solubility limit at the lower temperatures. In order to effectively maintain the interstitial oxygen in position, we have discovered that the temperature of the body 100 must be cooled during the rapid cooling step to about 400° C. at a rate exceeding 30° C./min. Thereafter, the time for reducing the body temperature from 400° C. to room temperature can be at a much slower rate without affecting the interstitial oxygen form of the lattice.

Reference is now made to FIG. 3 for a description of the measurement process. The sample body 100 of semiconductor material is heated to the predetermined temperature of 1300° C. The material is heated in any suitable apparatus known in the art. Accordingly, no further detailed explanation is needed of such apparatus.

The sample body 100 is then cooled to a temperature of about 400° C. at a rate greater than 30° C./min to maintain all of the oxygen in interstitial form. Thereafter, the sample body 100 is further cooled to ambient temperature such as a typical room temperature of 20° C.

The body 100 is then prepared to be substantially homogeneous in oxygen distribution with a defect-free surface as described above. The body 100 is then placed in position in the apparatus in FIG. 3 to measure the intensity of the absorption band related to the interstitial oxygen of the material. This is done by exposing the sample 100 to a beam 28 from an IR source 30. In the mode being described the beam is passed through the sample in the manner known in the art as the transmission mode. It should be understood, nevertheless, that the invention can be practiced by effecting reflection of the beam from the surface with suitable apparatus known in the art. However, at the present state of the art, it appears that the intensity of the reflection band is difficult to measure and for that reason the reflective mode of measuring the absorption band is not desirable.

With the sample moved to allow the beam 28 to pass directly to the monochromator, the monochromator receives the beam 28 at intensity $I_0$. The monochromator converts the broad spectrum IR beam to a preselected wavelength of about 9.0 cm wavelength. See the above-identified ASTM Standards and the Kaiser, et al. paper for a description of the wavelengths required to identify the absorption by interstitial oxygen.

Detector 38, responding to the monochromatic intensity signal beam, provides either a signal S or $S_0$ depending on whether it is a transmitted signal (I) or an incidence signal ($I_0$). Electronics 42 calculates the transmissivity T and applies it to the microprocessor 44 for determination of the absorption coefficient $\alpha$ and thus the oxygen concentration in accordance with equation (1) as described above in the ASTM Standards.

The oxygen concentration is represented by a signal that is applied on path 46 to a suitable device such as a display or memory 48. Repeated tests have shown that the oxygen concentration measured by this procedure is accurate and reproducible.

In order to determine the amount of noninterstitial form of oxygen that is contained in a given body of semiconductor material, a preliminary step to the process just described is required. As known in the art, the interstitial form of oxygen in a body of semiconductor material can be determined by the ASTM method described in the above-identified publications. Essentially, the ASTM method is implemented by the apparatus illustrated in FIG. 3. The essential and critical difference in the process of the present invention over that which has been described in the literature identified above as implemented by the ASTM method is in the condition or state of the sample being tested. In order to determine the noninterstitial oxygen in the sample, the first step involves following the procedures of the ASTM guidelines. In brief, the procedure is to expose the unheated sample in a transmissive mode to IR source 30 to develop the transmitted (I) and incidence ($I_0$) signals to the monochromator 34. The apparatus functions as described hereinabove to provide a signal on path 46 representing the oxygen concentration of interstitial oxygen only. It should be understood that the other oxygen forms in the body of material will not absorb the 9.0 $\mu$m IR energy passing through it. It is only by heating the body to the predetermined temperature such as 1300° C. for silicon as described hereinabove that causes the transformation of all of the oxygen existing in the body into interstitial form occurs.

The sample body 100 is then heated to the temperature needed to convert the oxygen to interstitial form as described hereinabove. The difference between the total oxygen content produced by the heating and cooling step of the specimen of sample body 100 is then compared to the oxygen concentration produced by the measurement of the sample at room temperature without the heat treatment. The difference between the total and interstitial oxygen values is the noninterstitial oxygen content in the semiconductor material.

In practice, the amount of interstitial oxygen of all of the oxygen that naturally exists in the material may range in the order of 20–80%. Moveover, the amount of oxygen precipitates and oxygen complexes may comprise anywhere from 20 to 80% of the oxygen in a semiconductor material. The amount of substitutional oxygen is usually quite low, in the order of less than 1% of the total oxygen in the material.

The process for thus determining in a given sample noninterstitial oxygen including oxygen precipitates and oxygen complexes is summarized as follows:

Step 1—Measure interstitial oxygen in a sample;

Step 2—Convert all of the oxygen in the sample to interstitial oxygen by heating to the minimum critical temperature and maintaining that temperature for a sufficient time to convert all the oxygen to interstitial form and thereafter cooling at a rate to maintain the oxygen in the interstitial form;

Step 3—Measure the interstitial oxygen in the treated sample;

Step 4—Subtract the measured value of Step 1 from the measured value of Step 3 to give the noninterstitial oxygen originally present oxygen in the sample before treatment.

Figure 4:
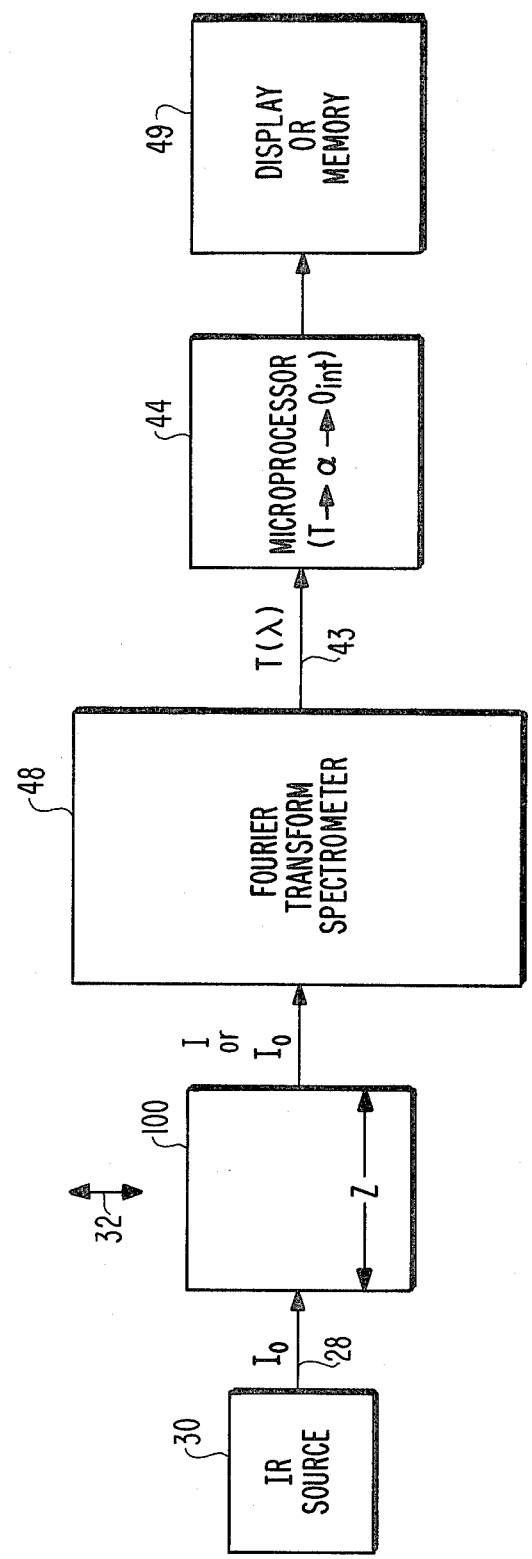
FIG. 4 is a block diagram of another and preferred form of a system for determining the oxygen content of material according to the invention.

In a preferred form of apparatus for practicing the invention, as shown in FIG. 4, the Fourier Transform Spectrometer with a microprocessor 44 and display or memory 48, provides more accurate and rapid transform of the IR beam 28 to a monochromatic optical signal in electrical form of the transmissivity (T) directly to the microprocessor 44 on path 43. A suitable monochromator for providing such functions is, for example, a FTS-15-Infrared Fourier Transform Spectrometer available from Digilab Inc., of Cambridge, Mass.

What is claimed is:

1. A method for determining all of the oxygen present in a body of essentially monocrystalline semiconductor material capable of containing interstitial oxygen identifiable by a well-defined absorption band, comprising the steps of:
   (a) heating the body to a first temperature to initiate the conversion of all of the oxygen present in said body to interstitial form and maintaining said first temperature for a time period sufficient to convert said oxygen to interstitial form;
   (b) cooling the heated body both to a second temperature and at a rate of cooling sufficient to maintain all of said oxygen in said interstitial form;
   (c) cooling said body still further to a third temperature corresponding to room temperature; and
   (d) thereafter measuring at said third temperature the intensity of the absorption band related to the interstitial oxygen of said material of said body to provide an intensity signal representing all of the oxygen contained in said body;
   (e) said measuring step comprising the step of exposing said material to a beam of infra-red (IR) energy and measuring the intensity of said absorption band after said exposure step to determine the absorption coefficient ($\alpha$) related to said interstitial oxygen;
   (f) said cooling rate and second temperature being determined by repeating steps (a) through (d) to determine the minimum cooling rate as indicated by no change in the measurement of interstitial oxygen;
   (g) said first temperature and time period being determined by repeating each of steps (a) through (d) until the measurement of interstitial oxygen remains constant.

2. The method according to claim 1, comprising, prior to said intensity measuring step, the step of:
   preparing said body for optical measurements by removing sufficient respective amounts of two opposed body surface layers so that said body is substantially homogenous in oxygen distribution with a defect-free surface.

3. The method according to claim 1, comprising prior to the step for heating said body the steps of:
   (a) measuring the intensity of the absorption band related to the interstitial oxygen of said material of said body to provide an intensity signal representing the interstitial oxygen content of said material;
   (b) thereafter performing the heating, cooling, and intensity measuring steps a-d, respectively, recited in claim 1; and
   (c) thereafter subtracting the magnitude of the interstitial oxygen content intensity signal from the total oxygen content intensity signal to provide a difference signal representing the oxygen content of said material that consists essentially of the noninterstitial oxygen, said noninterstitial oxygen content comprising substituted oxygen, precipitates and complexes, respectively, of oxygen and the semiconductor material.

4. The method according to claim 3, comprising, prior to the intensity measuring step (a) recited in claim 3, the step of:
   preparing said body for optical measurements by removing sufficient respective amounts of two opposed body surface layers so that said body is substantially homogenous in oxygen distribution with a defect-free surface.

5. The method according to claims 1, 2, 3 or 4, wherein said monocrystalline material is a body of silicon.

6. The method according to claims 1, 2, 3 or 4, wherein said monocrystalline material is a body of germanium.

7. The method according to claim 5, wherein said body is heated to a temperature of about 1300° C., for approximately one hour.

8. The method according to claim 5, wherein said body is cooled to a temperature of about 400° C. at a rate exceeding 30° C./min.

9. The method according to claim 1, wherein the irradiation by infrared radiation is performed in a transmission mode whereby the absorption coefficient is determined by detecting a beam that passes through said body.

10. The method according to claim 1, wherein the irradiation by infrared radiation is performed to determine the reflection of the beam from the surface of the body.

11. A method for determining the total oxygen content in a body of essentially monocrystalline semiconductor material capable of containing interstitial oxygen identifiable by a well-defined absorption band comprising the steps of:
    (a) converting all of the oxygen present in said body to interstitial form by heating the body to a temperature and maintaining said temperature for a time duration sufficient to convert all of the oxygen present in the body to interstitial form,
    (b) cooling said body to a lower temperature and at a rate to maintain said oxygen in interstitial form; and
    (c) determining the amount of interstitial oxygen in said body by measuring the intensity of the absorption band related to interstitial oxygen;
    (d) said measuring step comprising the step of exposing said material to a beam of infra-red (IR) energy and measuring the intensity of said absorption band after said exposure step to determine the absorption coefficient ($\alpha$) related to said interstitial oxygen.

* * * * *